United States Patent [19]
Sting

[11] Patent Number: 5,015,092
[45] Date of Patent: May 14, 1991

[54] SAMPLING PROBE FOR OPTICAL ANALYZATION OF A SAMPLE

[75] Inventor: Donald W. Sting, New Canaan, Conn.

[73] Assignee: Spectra-Tech, Inc., Stamford, Conn.

[21] Appl. No.: 347,829

[22] Filed: May 5, 1989

[51] Int. Cl.$^5$ .......................................... G01N 21/01
[52] U.S. Cl. ..................................... 356/300; 356/244
[58] Field of Search ...................... 356/244, 300, 410; 250/576

[56] References Cited

U.S. PATENT DOCUMENTS

| | | | |
|---|---|---|---|
| 3,362,224 | 1/1968 | Melone | 73/327 |
| 3,370,502 | 2/1968 | Wilks, Jr. | |
| 3,470,261 | 9/1969 | Roberts | 585/401 |
| 3,669,545 | 6/1972 | Gilby | 356/300 X |
| 4,175,864 | 11/1979 | Gilby | 356/244 X |
| 4,201,914 | 5/1980 | Perren | 250/341 |
| 4,582,809 | 4/1986 | Block et al. | 250/365 X |
| 4,595,833 | 6/1986 | Sting | 250/353 |
| 4,602,869 | 7/1986 | Herrick | 346/244 |
| 4,730,882 | 3/1988 | Messerschmidt | 350/96.1 |
| 4,747,687 | 5/1988 | Hoppe et al. | 356/410 X |

FOREIGN PATENT DOCUMENTS 55-101848  8/1980  Japan ................................. 250/341

Primary Examiner—Vincent P. McGraw
Attorney, Agent, or Firm—Calfee, Halter & Griswold

[57] ABSTRACT

A sampling probe for optical analyzation of a sample includes an MIR element having a cylindrical body with a flat end and a curved end. The flat end and the adjacent active portion of the body is positioned against the sample, and the curved end is operative to receive and emit radiant energy internally multiply reflected in both directions along the MIR element to optically analyze the sample. For high pressure and/or high temperature applications, the MIR element is preferably a crystal partially mounted in and sealed to a holder, which in turn is mounted in and sealed to one wall of a fluid or reaction chamber. The crystal or adjacent holder surface is coated or mirrored to enhance optical efficiency, and the crystal is secured within and sealed to the holder by soldering, an adhesive bond or a prestressed friction fit. The sampling probe includes an optical system having a radiant energy beam splitter and inlet and egress optics for the MIR element, the inlet and egress optics being selected from reflaxicon optics, an objective lens, cooperative mirror pairs or spherical or ashperical optics.

17 Claims, 4 Drawing Sheets

SAMPLING PROBE FOR OPTICAL ANALYZATION OF A SAMPLE

BACKGROUND OF THE INVENTION

1. Field of the Invention

The present invention relates to a sampling probe for a sample contained in a high pressure and high temperature fluid or reaction chamber, the sampling probe utilizing a multiple internal reflection (MIR) element having a cylindrical body with a reflective end and a curved end. The reflective end and an adjacent active portion of the probe body are positioned against or in the sample. The sampling probe is easily removed from and accurately reinstalled in the fluid or reaction chamber.

2. Description of Prior Art

This invention principally relates to a non-destructive reaction monitoring probe preferably using infrared spectroscopy. The invention utilizes an optics system operative to internally reflect source infrared radiation a number of times off an MIR element surface in contact with the fluid or sample under analysis and then to direct the remaining radiation (as modified by the infrared absorbtion characteristics of the fluid or sample) to a detector for analysis of the fluid or sample. Specifically, the invention is preferably directed to an optical system including a probe extending into the reaction chamber for IR spectroscopic analysis and monitoring of reactions being conducted under or fluids being subjected to elevated pressures and/or temperatures.

In the the infrared range, practically all organic (and many inorganic) molecules have characteristic spectra that positively identify them. In one such identification method, infrared energy is reflected along the length of the crystal by the physical phenomenon of total internal reflection. A fluid sample or reaction placed in contact with the crystal selectively absorbs different frequencies of IR energy from the crystal. The energy that is not absorbed exits the crystal and is directed to a detector which measures the distribution of energy absorbed by the fluid or reaction so as to obtain and display its infrared spectra. Sting U.S. Pat. No. 4,595,833 (assigned to the assignee of the present invention), Messerschmidt U.S. Pat. No. 4,730,882 (assigned to the assignee of the present invention) and Gilbey U.S. Pat. No. 3,669,545 illustrate different systems for employing an MIR crystal to analyze a fluid or solid in contact therewith.

Sting U.S. Pat. No. 4,595,833 discloses reflaxicon optics for directing infrared radiation from a source into the cone shaped entry end of a cylindrically shaped MIR crystal. The non-absorbed radiant energy leaves the cone shaped exit end of the MIR crystal and is transmitted through additional reflaxicon optics toward a detector. The cylindrically shaped MIR element is sealed into a tubular member in order to provide a sample chamber or cell for the fluid and fluidized samples being analyzed.

Messerschmidt U.S. Pat. No. 4,730,882 discloses an elongated flat MIR crystal having a first surface, a slightly longer second surface and beveled entry and exit end surfaces interconnecting the same. The radiant energy enters at right angles through the second surface, reflects off the beveled entry surface, reflects between the second and first surfaces in multiple reflections along the length of the crystal and reflects off the beveled exit end surface through the second surface to a detector.

The circular MIR crystal of U.S. Pat. No. 4,595,833 and the flat, beveled ended MIR crystal of U.S. Pat. No. 4,730,882 have been successfully commercially sold in sampling assemblies to analyze fluids and solids. These MIR crystal elements require special assembly, disassembly and maintenance procedures within the analysis chamber. These MIR crystals, as currently mounted, are not preferred for high pressure and/or temperature fluid monitoring because of the possibility of the MIR crystal breaking. In addition, the crystals, as currently mounted, are positioned in the chamber presenting obstructions to mixing or fluid flow.

Gilbey U.S. Pat. No. 3,669,545 discloses a crystal MIR probe used prior to the Gilbey patent application as well as the crystal MIR probes disclosed by Gilbey. The prior art MIR crystal probe is illustrated in FIG. 1 of Gilbey and includes a rectangular body having a 90° "roof" at one end and a flat surface at its other end. The 90° "roof" end provides (a) an angled, flat entry surface to admit infrared energy for multiple internal reflections along the MIR crystal and (b) an oppositely angled, flat exit surface for emitting the infrared energy that has been reflected back. Therefore, the prior art MIR crystal disclosed in Gilbey provides entry and exit of the infrared energy from the opposed flat sides of the "roof" at the same end of the rectangular crystal.

The MIR crystal designs proposed by Gilbey include a rectangular body having beveled or angled ends. The infrared energy enters one side of the body and is reflected off one beveled end of the body in alignment therewith for multiple internal reflections along that body. The radiant energy is reflected off the other crystal end and is then multiply reflected in the opposite direction for return to and exit from the same beveled face. All embodiments of the Gilbey patent disclose a class of crystals in which one face serves simultaneously to both totally reflect entering energy into the crystal and transmit exiting energy out of the crystal.

All of the rectangular MIR crystal bodies disclosed in the Gilbey patent are difficult to seal, particularly in high pressure and/or high temperature applications. The hole through the holder must be broached or a multiple piece holder used. In addition, the rectangular crystal bodies are not easily mounted in or removed from the reaction cell and reassembly requires both precise positioning and orientation of the crystal for accurate spectroscopic measurements.

SUMMARY OF THE INVENTION

The principal object of the present invention is to provide an MIR crystal probe adapted to analyze fluids or reactions in general and those fluids or reactions under high pressure and/or temperature in particular. This object is accomplished by utilizing an MIR probe having a cylindrical body, a reflective end and a curved end. The reflective end and an immediately adjacent active portion of the crystal body is in contact with or immersed in a sample, preferably a fluid or reaction. The MIR element is preferably a crystal having a flat surface as its reflective end and a conical surface as its curved end.

It is another object of the present invention to provide a cylindrical MIR crystal probe which can be temporarily removed and accurately reinstalled for maintenance purposes and/or can be easily and accurately replaced with a different crystal to vary the optical path length. This object is accomplished by mounting the MIR crystal element in a holder assembly threadably installed in and removed from a wall of the fluid or reaction chamber. The holder assembly preferably includes a holder plug and a cooperating retainer nut. The holder plug has a bore therethrough to which a portion of the crystal is secured and sealed. The retainer nut has a bore therethrough which removably receives the holder plug. The retainer nut has external threads therealong cooperating with a threaded socket in the wall of the fluid chamber, whereby the holder assembly can be screwed into installed condition. A beveled cam surface on the retainer nut engages a radially outwardly extending shoulder on the received holder plug to urge the latter into a sealed engagement fit with the wall of the fluid chamber.

It is still another object of the present invention to provide a fluid tight seal of the MIR crystal to the holder assembly while optimizing the reflected transmission of the radiant energy along the crystal element to and from the active area of the crystal positioned within the sample. For this purpose, one surface of either the mounting portion of the crystal or the receiving bore in the holder assembly is either mirrored or coated with a non-absorbing material. The mounting portion of the crystal can be secured and sealed to the holder assembly by adhesive, soldering or a prestressed friction fit.

It is yet another object of the present invention to provide optics for directing radiant energy from a source to the curved end of the crystal for multiple internal reflections therealong to the reflective end and then back along the element through the curved end of the crystal to a detector. The optics includes either a reflective or refractive beam splitter coupled with reflaxicon optics, an objective lens, cooperating concave mirror pairs or spherical or aspherical optics.

These and other objects and advantages of the present invention will become apparent as the following description proceeds.

DETAILED DESCRIPTION OF THE PREFERRED EMBODIMENTS

Figure 1:
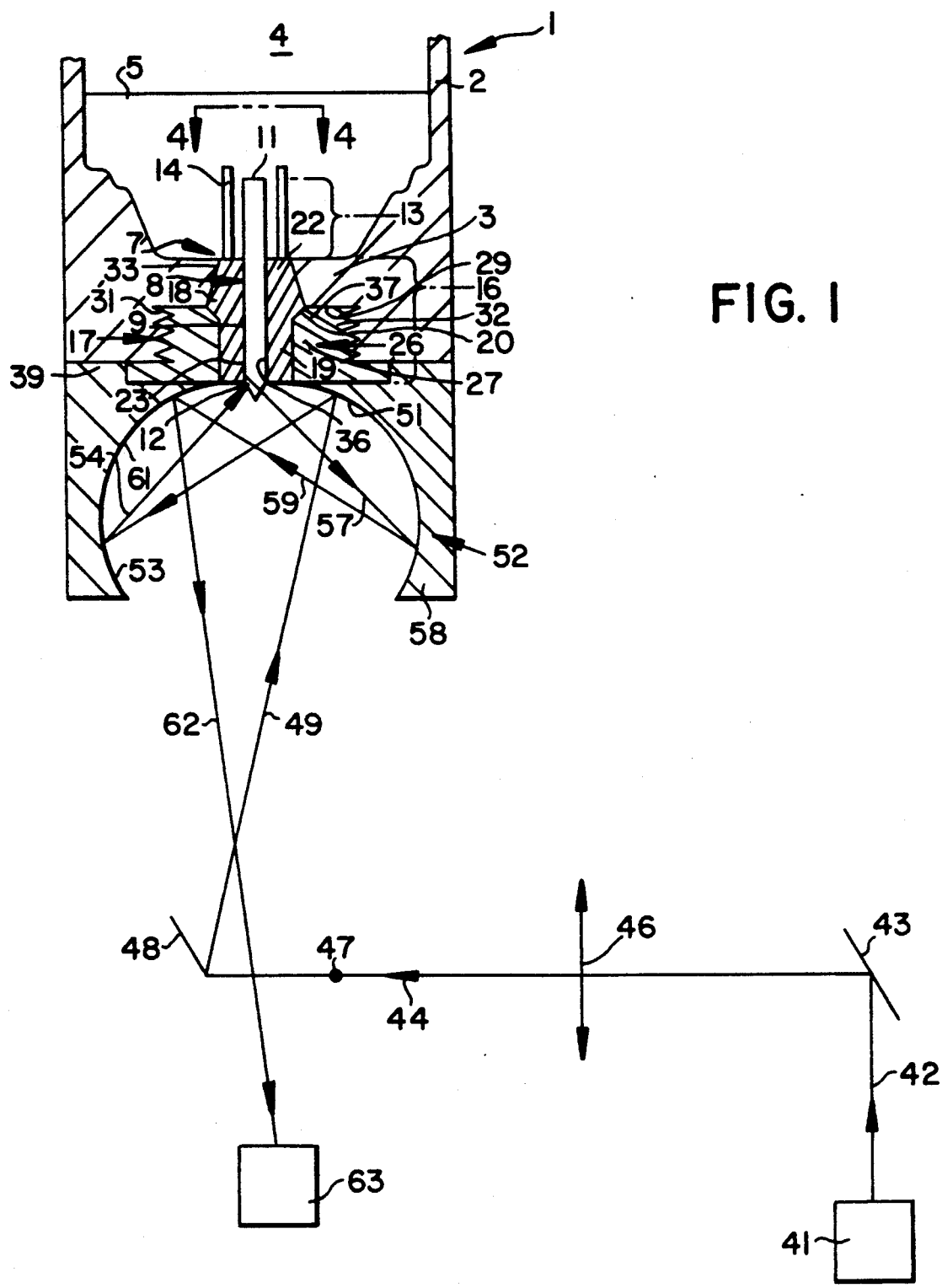
FIG. 1 is an elevation of the sampling probe of the present invention with the optics being schematically illustrated and with the reaction chamber being shown in cross-section for ease and clarity of illustration.

Turning now in more detail to the drawings and initially to the embodiment illustrated in FIG. 1, a fluid or reaction chamber body, indicated generally at 1, preferably includes a cylindrical sidewall 2 and a base wall 3. Although not illustrated, the chamber body 1 either has an integral or removable top wall cooperating with the cylindrical sidewall 2 and base wall 3 to define an enclosed cavity 4. This cavity forms a sealed fluid chamber in which fluids or reactions 5 can be contained and continuously analyzed.

For this latter purpose, an MIR probe, indicated generally at 7, is positioned in and extends through one wall of the fluid or reaction chamber 1. As illustrated, the MIR probe 7 is mounted in and extends through the bottom wall 3 of the reaction chamber, but alternatively could be mounted in and extend through the side or top wall thereof. The MIR probe 7 includes an elongated multiple internal reflection (MIR) element, indicated generally at 8. Although a crystal rod is preferred as the MIR element, the invention also contemplates using other MIR elements, such as a fiber optics rod.

The MIR crystal 8 includes a cylindrical body 9 having a reflective end 11 and a curved end 12. The reflective end 11 of the MIR crystal 8 is preferably a flat surface as illustrated in FIG. 1, although aluminized or gold coated flat or curved surfaces could be used for providing the required MIR reflectivity. The reflective end 11 and an adjacent active portion 13 of the MIR crystal 9 are positioned against or immersed in the sample 5, preferably a fluid or reaction.

Figure 4:
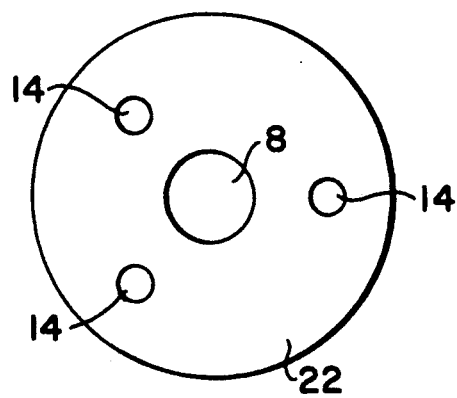
FIG. 4 is a plan view taken substantially along the plane 4—4 in FIG. 1 illustrating the circumferentially spaced protective pins surrounding the active portion of the cylindrical MIR crystal.

The active portion 13 of the MIR crystal 8 is surrounded by a plurality of circumferentially spaced protective pins 14. As shown in FIG. 4, three protective pins 14, spaced at 120° circumferential increments, can be provided. These pins limit access to the active portion 13 of MIR crystal 8 and thus protect the same against breakage or improper handling.

The active portion 13 of the crystal is retained in its position within the sample 5 by the mounting portion 16 of the MIR crystal 8 being secured and sealed to a holder assembly, indicated generally at 17. The holder assembly 17 includes a holder plug 18 having a bottom cylindrical section 19, a radially outwardly tapered shoulder 20 and an upper sealing section 22 tapered radially inwardly from bottom to top, as illustrated in FIG. 1. The holder plug 18, preferably a high strength material with good chemical resistivity properties, such as stainless steel, has a cylindrical bore 23 extending therethrough coaxial with the center line of the holder plug. The mounting portion 16 of MIR crystal 8 is secured and sealed to such bore 23 in a manner to enhance optical efficiency and to retain the sealed integrity of the cavity 4 of reaction or fluid chamber 1.

Several different structural and functional approaches to obtain the sealed mount may be utilized to achieve the desired objectives. For example, one surface of either the mounting portion 16 of the crystal body or the bore 23 through holder plug 18 can be mirrored to enhance the efficiency of the multiple internal reflections through the mounted portion of crystal 8. With one of such surfaces mirrored, the mounting portion 16 of the MIR crystal 8 is secured and sealed to the holder plug 18 by adhesive, soldering or a prestressed friction fit. In this latter regard, the O.D. of the crystal mounting portion and the I.D. of the holder plug bore are machined to close tolerances, with the crystal being inserted therein after the holder plug has been heated for slight expansion. Upon cooling, the holder plug bore tightly frictionally embraces the mounting portion 16 of the crystal 8 to provide a sealed, prestressed friction fit therebetween.

Alternatively, one surface of either the crystal mounting portion or the holder plug bore can be coated with a thin layer of non-absorbing material, having a lower index of refraction than the crystal. For example, the thin layer or coat could be a KBr material. With one of the surfaces thus coated, the mounting portion 16 of the crystal 8 would be secured and sealed to the inner diameter of the holder plug bore by adhesive (preferably an epoxy adhesive), soldering or a prestressed friction fit as described above.

The length of the MIR crystal 8 is selected according to the parameters required for the sample or reaction being analyzed. In other words, the MIR crystal length depends upon the mounting length 16 needed for stability purposes and the active area length 13 required for the analyzation being conducted. The holder plug with the crystal rod secured and sealed thereto (as required for the application) can then be inserted into the retainer nut 26 of the holder assembly 17.

Figure 2:
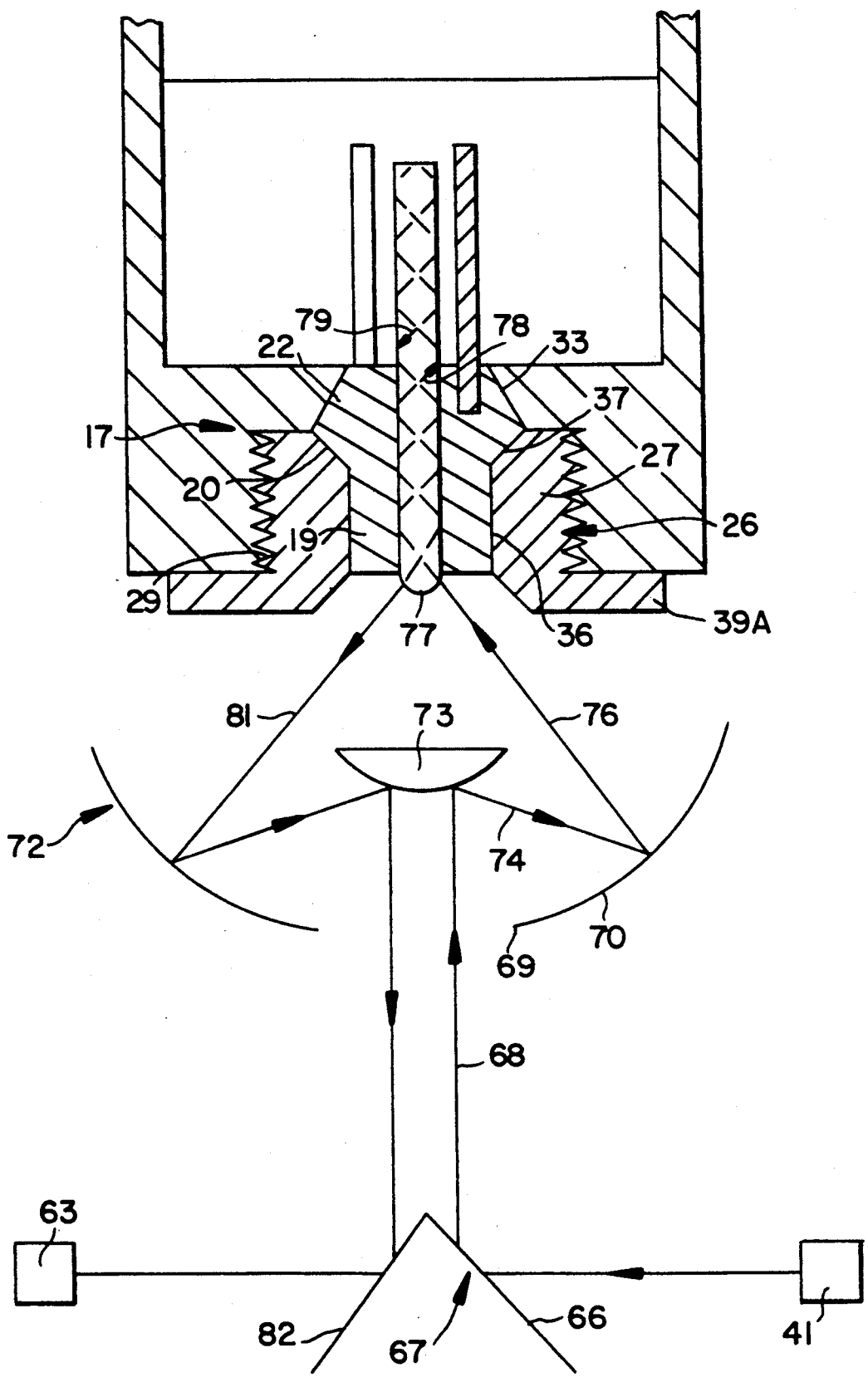
FIG. 2 is an elevation similar to FIG. 1 showing another embodiment for the MIR crystal and system optics.

The retainer nut 26 includes an upper shank 27 having an external flight of threads 29. These threads 29 cooperate with internal threads 31 on the inner diameter of a generally cylindrical socket 32 in base wall 3. Such base wall has a tapered annular seat 33 formed therein by a bore extending from the socket 32 to the cavity 4. The annular seat 33 is tapered radially inwardly from bottom to top as illustrated in FIGS. 1 or 2. The sealing surface 33 is tightly engaged by the complementally tapered outer surface of the sealing portion 22 of holder plug 18 to form a fluid tight seal therebetween.

For this purpose, the shank 27 of the retainer nut 26 has a bore 36 extending therethrough. At its upper end, an annular ferrule or radially outwardly tapered camming surface 37 is provided. For assembly, the holder plug 18 with the MIR crystal 8 mounted therein is removably positioned in the bore 36 of retainer nut 26, with the shoulder 20 on the holder plug engaging the cam surface 37 on the retainer nut.

The retainer nut is then screwed into the threaded socket 32 in the base wall 3 of the fluid or reaction chamber 1 to drive the sealing portion 22 of the holder plug into surface engagement with annular sealing surface 33 of the base wall. The retainer nut is advanced until the end of the shank 27 engages the end of the socket 32 and/or the flange 39 on the retainer nut engages the bottom of base wall 3. In such position, a fluid tight seal is formed between the holder plug and the base wall of the reaction cell 1.

It will be appreciated that the retainer nut 26 may be used with a number of different MIR crystals mounted in identically configured holder plugs 18. The crystal can be easily removed from the fluid or reaction chamber by unscrewing the retainer nut. The active portion of the crystal may be cleaned or polished and then reinstalled in the reaction cell by threading the holder assembly back into the threaded socket. Alternatively, a different crystal having different optical characteristics can be installed in the chamber by changing the holder plug and crystal utilized with the retainer nut. The threaded advancement of this retainer nut seals the selected holder plug and crystal to the chamber wall for optical analyzation of the fluid or reaction 5. For this purpose, many different optical systems can be utilized, with representative embodiments being disclosed in FIGS. 1 through 3 and 5.

Turning first to FIG. 1, the optical system includes a source 41 of radiant energy, preferably infrared energy. The beam of radiant energy 42, illustrated for simplicity by the beam centerline only, is reflected off angled mirror 43 in the direction of arrow 44. Additional transfer optics, comprising one or more mirrors, lenses or combinations thereof as symbolically illustrated by double arrow 46, focuses the radiant energy at first image plane 47. One-half of the diverging beam of incident radiant energy from the first image plane 47 is reflected off an angled intercepting mirror 48 positioned at an aperature image plane. The radiant energy 49 reflected from intercepting mirror 48 is directed to and reflected off concave mirror surface 51 forming part of the integral optics, indicated generally at 52. The reflected radiant energy from mirror 51 is directed to and reflects off of the opposed concave mirror 53 of the integral optics. The reflected incident energy 54 then enters the conical entry end 12 of MIR crystal 8.

The infrared energy entering the cylindrical body portion of the MIR crystal is multiply internally reflected upwardly along the crystal 8 until it is reflected off the flat end 11. The infrared energy then multiply internally reflects downwardly through the MIR crystal until it leaves the curved conical end 12 of crystal 8. Certain frequencies or bands of radiant energy are absorbed by the reaction or fluid 5 when the radiant energy beam is reflected off the active portion 13 of the crystal in contact therewith.

The remaining portion of the radiant energy reaching the curved conical end 12 is directed along path 57 to concave mirror 58 in alignment therewith. The returning radiant energy 59 is reflected off mirror 58 and is then directed to opposed concave mirror 61. The reflected radiant energy 62 from concave mirror 61 passes mirror 48 and is directed to a detector 63.

From the frequencies or bands of radiant energy remaining in the radiant energy beam leaving the crystal, the detector 63 determines the distribution of frequencies or energy bands of infrared energy absorbed by the sample 5 in cavity 4 to provide a fingerprints or identities of the components of the sample. This determination can be displayed with an infrared spectrum. The reaction or fluids being analyzed can be continuously monitored if desired, with the infrared spectra being successively displayed or the information being successively recorded and analyzed.

The accuracy of the optical analysis obtained is enhanced by the system illustrated in FIG. 1. Specifically, by utilizing a holder assembly, the active portion of the crystal can be accurately and repetitively positioned in the cavity 4 of the reaction cell 1 because of the threaded connection of the holder assembly to the body of the reaction cell and because of the precise configuration of the parts thereof. In addition, by having the inlet and exit optics integrally formed as an extension of the retainer nut 26 (as illustrated in FIG. 1), the optics are accurately positioned relative to the curved crystal end because of the integral construction and threaded connection.

Figure 3:
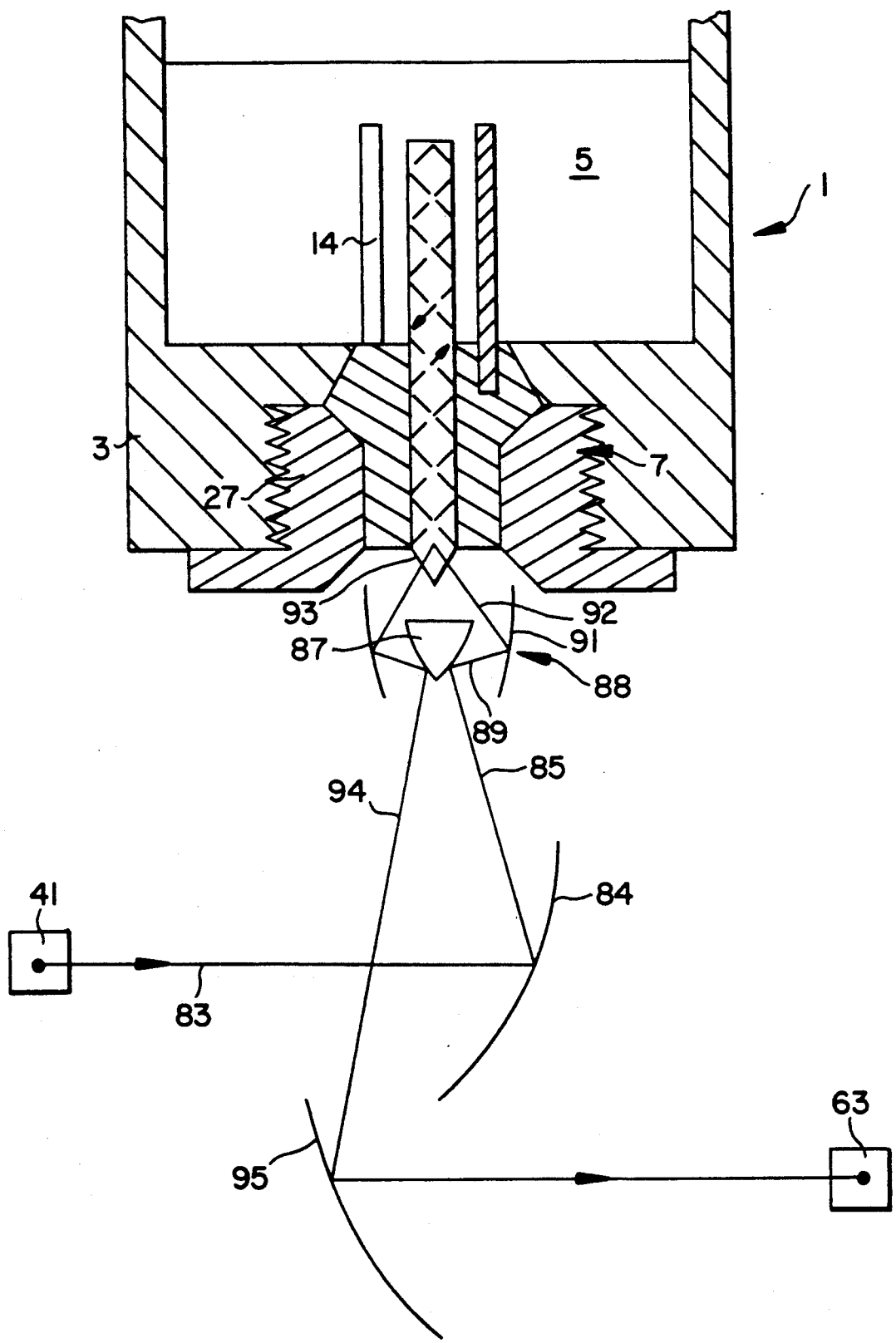
FIG. 3 is another elevation similar to FIG. 1 showing yet another embodiment for the MIR crystal and system optics.
Figure 5:
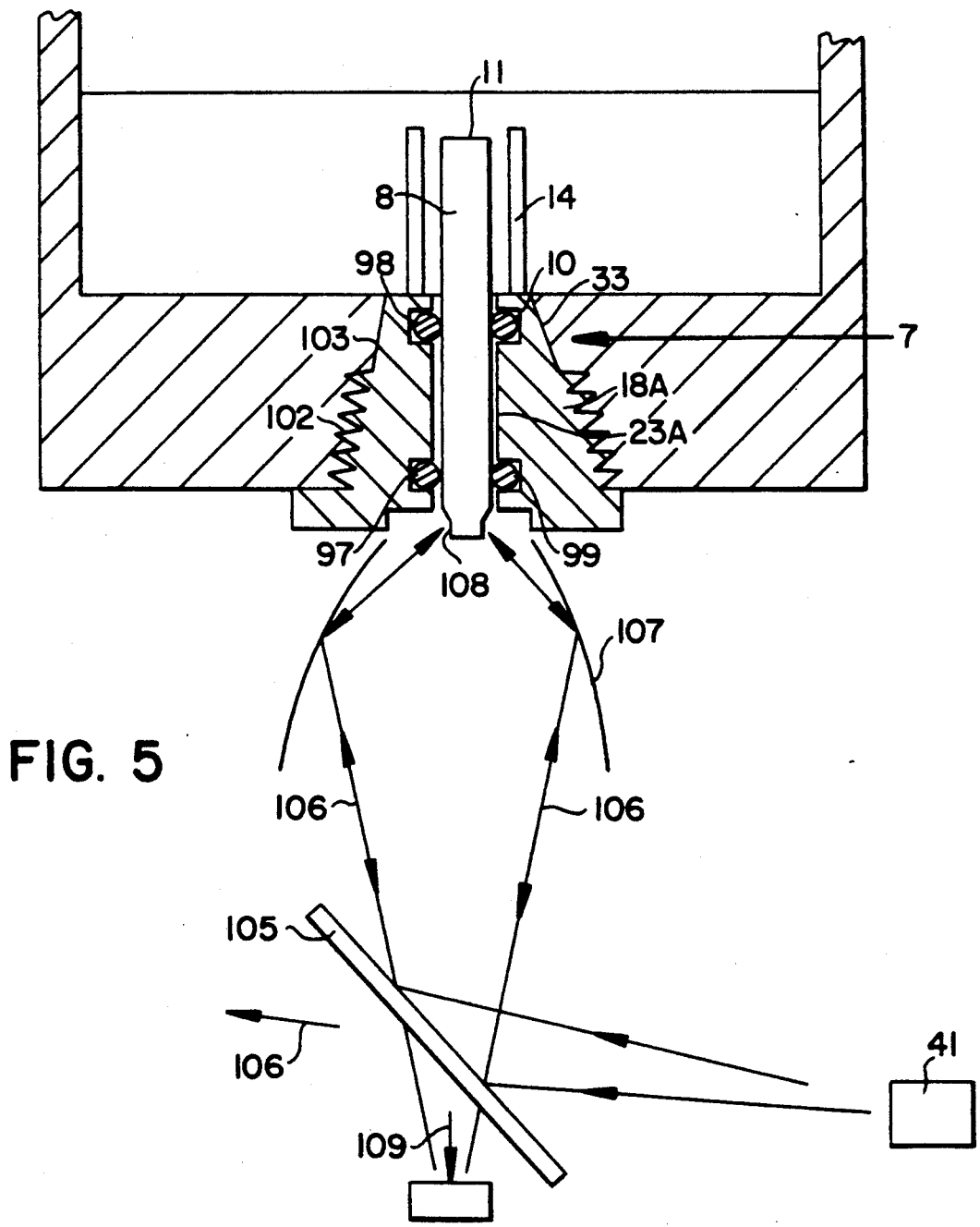
FIG. 5 is still another elevation similar to FIG. 1 showing another embodiment of the MIR crystal and system optics, with the MIR crystal being mounted in and sealed to the holder assembly for analyzing a low pressure and/or low temperature fluid.

Turning now to the additional embodiments illustrated in FIGS. 2, 3 and 5, like parts in these additional embodiments have been identified by like numerals to those used in FIG. 1. Turning initially to FIG. 2, the retainer nut 26 does not have a body extension providing integral optics. Instead, the retainer nut has a radially outwardly extending flange 39A which engages the bottom surface of base wall 3 when fully screwed into that base wall. As in the first embodiment, the retainer nut 39A thus accurately positions the holder plug 18 and MIR crystal 8 relative to the cavity 4 to enhance the efficiency of the optics employed.

In this embodiment, the radiant energy from source 41 is reflected off an incident mirror 66 of a beam splitter, indicated generally at 67. The reflected incident radiant energy 68 passes through a central hole 69 in primary mirror 70 of an objective lens, indicated generally at 72. The incident radiant energy beam 68 is reflected off the convex secondary mirror 73 of the objective lens back toward the primary mirror 70, as indicated at 74. The incident radiant energy 76 reflected off the primary mirror 70 enters the hemispherical curved end 77 of MIR crystal 8.

As in the FIG. 1 embodiment, the entering radiant energy is multiply internally reflected upwardly along the crystal 8, as schematically indicated by arrow 78. The non-absorbed returning radiant energy reflected off the flat end of crystal 8 multiply internally reflects downwardly therealong, as schematically indicated by the arrow 79. The returning radiant energy 81 is emitted from the crystal 8 through the hemispherical end 77. This returning radiant energy 81 is successively reflected off primary mirror 70, secondary mirror 73 and an outlet mirror 82 on beam splitter 67. The returning radiant energy reflected from outlet mirror 82 is directed to a detector 63 for fluid or reaction analyzation as described above.

Turning now to FIG. 3, a beam of radiant energy 83 from radiant energy source 41 is reflected off a first aspherical mirror 84. The incident radiant energy 85 reflected from first mirror 84 is directed to and reflected off a reflecting cone or secondary mirror 87 of reflaxicon optics, indicated generally at 88. The radiant energy 89 reflected from secondary mirror 87 is reflected off an annular toroidal mirror 91, constituting the primary mirror of the reflaxicon optics. The incident radiant energy beam 92 from primary mirror 91 enters the convex, toroidally shaped curved end 93 of MIR crystal element 8.

After multiple internal reflections upwardly and downwardly along the crystal element 8 (as described above), the returning radiant energy leaves the crystal element 8 through the toroidally shaped curved end 93 of crystal 8. The returning radiant energy 94 is sequentially reflected off primary toroidal mirror 91, secondary mirror 87 and second aspherical mirror 95. First and second aspherical mirrors 84 and 95, respectively, are positioned relative to one another and relative to the centerline of secondary conical mirror 87 to act as a beam splitter. The returning radiant energy is reflected off second aspherical mirror 95 to detector 63 for monitoring and analyzation of the fluid or reaction 5, as described above.

Turning now to FIG. 5, the MIR probe illustrated is principally designed for monitoring low pressure and/or low temperature samples. For this purpose, the elongated MIR crystal element 8 is secured and sealed to a holder plug 18A having a slightly different configuration than the holder plug 18 illustrated in FIGS. 1 through 3.

In this regard, the holder plug 18A includes a bore 23A extending centrally therethrough. The bore 23A has two vertically spaced annular grooves 97 and 98 provided therein. 0-ring seals 99 and 100 are respectively mounted in grooves 97 and 98. These 0-ring seals tightly embrace the mounting portion of the MIR crystal to secure such crystal to the holder plug 18A and to provide vertically spaced, fluid tight seals therebetween.

The annular external sidewall of holder plug 18A has a bottom threaded section 102 and a tapered top sealing section 103. The threaded section 102 of the holder plug cooperates with threads 31 on socket 32 in the base wall 3 of the fluid or reaction chamber 1. When the holder plug 18A has been fully screwed into the socket 32, the tapered sealing surface 103 thereof is in flush engagement with the sealing surface 33 on base wall 3 to provide a fluid tight seal therebetween. This threaded and sealed connection for a low pressure and/or low temperature reaction or fluid accurately positions the MIR crystal 8 relative to the optics employed.

In this embodiment, the optics include a radiant energy source 41 directing a beam of radiant energy toward a refractive beam splitter 105. Approximately 50% of the incident radiant energy is transmitted through the refractive beam splitter 105, as schematically illustrated by 106. The remaining part of the incident radiant energy beam is reflected off the refractive beam splitter 105 as indicated by the arrows 106. This incident radiant energy is reflected off annular aspherical mirror 107 toward the curved end of the MIR crystal.

In this embodiment, the curved end of the MIR crystal is illustrated as a concave, truncated toroid 108. The incident radiant energy passes through the entire curved surface 108, is multiply internally reflected upwardly through the crystal 8 and is then reflected off the flat or reflectively coated crystal end 11. The radiant energy that is not absorbed by the sample 5 from the active portion of the crystal 8 is then multiply internally reflected downwardly through the crystal 8. The returning reflected radiant energy passes through the entire truncated toroidal end 108. This returning radiant energy is then reflected off annular aspherical mirror 107 and passes through the refractive beam splitter 105, as indicated by the arrow 109. Such radiant energy is directed to a detector 63 for continuous monitoring and/or analyzation of the sample as described above.

It will be apparent from the foregoing that changes may be made in the details of construction and configuration without departing from the spirit of the invention as defined in the following claims. For example, any suitable optical system, as illustratively depicted, for example, in FIGS. 1 through 3 and 5, could be utilized with any suitable curved end shape of MIR crystal having any selected length or diameter, as generally illustrated in the same figures. In addition, the MIR crystal selected can be mounted in any holder plug or holder assembly and can be secured and sealed thereto in any suitable manner, including the exemplary ways described above.

I claim:

1. A sampling probe for optically analyzing a sample comprising
    a source of radiant energy;
    an MIR optical element having a cylindrical body including a flat end and a curved end, the flat end and an adjacent active portion of the cylindrical body being positioned against the sample, the MIR element being partially mounted in and sealed to a hole in a holder means; and
    optical means to direct radiant energy from the source to the curved end for multiple internal reflections along the element to the flat end and then back along the element through the curved end to a detector, the optical means including a beam splitter and radiant energy inlet and removal means selected from mirror elements integrally forming a part of the holder means.

2. The sampling probe of claim 1 further including a high pressure and/or high temperature reaction chamber enclosing the sample, and the holder means is secured in and sealed to one wall of the reaction chamber.

3. The sampling probe of claim 2 wherein the holder means includes a holder plug and a retainer nut, the hole receiving the MIR element being a first bore through the holder plug.

4. The sampling probe of claim 3 wherein the retainer nut has both a threaded external section cooperating with threads in the reaction chamber wall and a second bore selectively receiving the holder plug, the second bore having a beveled cam surface therein engaging a radially outwardly extending shoulder on the holder plug to push that holder plug into a sealed relationship with the retainer wall as the retainer nut is threaded into the retainer wall.

5. The sampling probe of claim 2 wherein one surface of either the hole or a mounting portion of the MIR element body is mirrored, and the MIR element is secured to the holder by adhesive, prestressed friction fit or soldering.

6. The sample probe of claim 2 wherein one surface of either the hole or MIR element body is coated with a thin layer of non-absorbing material ;having a lower index of refraction than the crystal, and the MIR element is secured to the body by adhesive, prestressed friction fit or soldering.

7. The sampling probe of claim 1 wherein the MIR element is a crystal, and the curved end has a concave or convex arcuate shape selected from a group of shapes consisting of a cone, a hemisphere, a toroid or truncations thereof.

8. The sampling probe of claim 1 wherein circumferentially spaced protective pins are mounted in the holder means and extend therefrom to surround and protect the active portion of the MIR element.

9. The sampling probe of claim 1 wherein the radiant energy inlet and removal means are selected from reflaxicon optics, an objective lens, cooperative mirror pairs or spherical or aspherical optics.

10. The sampling probe of claim 9 wherein the MIR element is a crystal.

11. The sampling probe of claim 1 wherein the MIR optical element is a fiber optic rod.

12. The sampling probe of claim 1 wherein the holder means comprises a holder plug threaded into a wall of a reaction chamber containing the sample and the MIR optical element is partially mounted in and sealed to a bore through the holder plug by spaced 0-ring seals carried by the holder plug.

13. A sampling probe for optically analyzing a sample comprising:
a source of radiant energy;
a reaction chamber enclosing the sample;
an MIR optical element having a cylindrical body, a reflective end and curved end, the reflective end and an adjacent active portion being positioned against the sample;
a holder assembly for the MIR element providing a selectively removable, sealed mount of the MIR element to the reaction chamber, the holder assembly including a holder plug and retainer member; and optical means to direct radiant energy from the source to the curved end of the MIR optical element for multiple internal reflections along the element to the reflective end and then back along the element through the curved end to a detector, the optical means to direct being an integral part of the retainer member.

14. The sampling probe of claim 13 wherein the reflective end is flat and the holder plug has a hole therethrough to which a mounting portion of the MIR element is secured and sealed and the retainer member selectively receives the holder plug and can be selectively advanced to form a seal between the holder assembly and reaction chamber.

15. The sampling probe of claim 13 wherein the reflective end is coated.

16. A sampling probe for optically analyzing a sample comprising
a source of radiant energy;
an MIR optical element having a cylindrical body including a flat end and a curved end, the flat end and an adjacent active portion of the cylindrical body being positioned against the sample, the MIR optical element being at least partially mounted in and sealed to a holder means, which in turn is secured in and sealed to one wall of the reaction chamber;
the holder means including a holder plug and a retainer nut, a mounting portion of the cylindrical MIR body being received in and sealed to a first bore through the holder plug;
the retainer nut having both a threaded external section cooperating with threads in the reaction chamber wall and a second bore selectively receiving the holder plug, the second bore having a beveled cam surface therein engaging a radially outwardly extending shoulder on the holder plug to push the holder plug into a sealed relationship with the retainer wall as the retainer nut is threaded into the retainer wall; and
optical means to direct radiant energy from the source to the curved end for multiple internal reflections along the element to the flat end and then back along the element through the curved end to a detector.

17. A sampling probe for optically analyzing a sample comprising
a reaction chamber containing the sample;
an MIR optical element having a cylindrical body including a flat end and curved end, the flat end and an adjacent active portion of the cylindrical body being positioned against the sample;
holder means to mount the MIR element to the reaction chamber, the holder means including
a holder plug having a bore at least partially therethrough to which at least a portion of the cylindrical body of the MIR optical element is secured and sealed and
a retainer member removably secured to a wall of the reaction chamber and supporting and sealing the holder plug in position;
a source of radiant energy and
optical means to direct radiant energy from the source to the curved end of the MIR element for multiple internal reflections along the MIR element to the flat end and then back along the MIR element through the curved end to a detector.

* * * * *